(12) United States Patent
Hitschmann et al.

(10) Patent No.: US 10,779,994 B2
(45) Date of Patent: Sep. 22, 2020

(54) COMPRESSION DEVICE

(71) Applicant: 3M INNOVATIVE PROPERTIES COMPANY, Saint Paul, MN (US)

(72) Inventors: Guido Hitschmann, Neuss (DE); Tim Jaeger, Schwenningen (DE); Magdalena R. Jüngst, Munich (DE); Berenike I. Sauer, Waiblingen (DE)

(73) Assignee: 3M Innovative Properties Company, Saint Paul, MN (US)

( * ) Notice: Subject to any disclaimer, the term of this patent is extended or adjusted under 35 U.S.C. 154(b) by 248 days.

(21) Appl. No.: 15/579,959

(22) PCT Filed: Jun. 9, 2016

(86) PCT No.: PCT/US2016/036582
§ 371 (c)(1),
(2) Date: Dec. 6, 2017

(87) PCT Pub. No.: WO2016/201035
PCT Pub. Date: Dec. 15, 2016

(65) Prior Publication Data
US 2018/0221213 A1 Aug. 9, 2018

(30) Foreign Application Priority Data
Jun. 9, 2015 (EP) .................................... 15171126

(51) Int. Cl.
*A61F 13/08* (2006.01)
*A61F 13/00* (2006.01)

(52) U.S. Cl.
CPC .... *A61F 13/085* (2013.01); *A61F 2013/0028* (2013.01); *A61F 2013/00127* (2013.01); *A61F 2013/00148* (2013.01)

(58) Field of Classification Search
CPC .......... A61F 13/085; A61F 2013/00127; A61F 2013/00148; A61F 2013/0028;
(Continued)

(56) References Cited

U.S. PATENT DOCUMENTS

| 3,538,914 A | 11/1970 | Myers |
| 4,090,508 A * | 5/1978 | Gaylord, Jr. .......... A61F 5/0106 602/26 |

(Continued)

FOREIGN PATENT DOCUMENTS

| DE | 202009010745 | 1/2011 |
| WO | WO 2000-15139 | 3/2000 |

(Continued)

OTHER PUBLICATIONS

International Search Report for PCT International Application No. PCT/US2016/036582, dated Sep. 7, 2016, 5 pages.

*Primary Examiner* — Rachael E Bredefeld
*Assistant Examiner* — Camtu T Nguyen
(74) *Attorney, Agent, or Firm* — 3M Innovative Properties Company; Trisha D. Adamson (57) ABSTRACT

Compression device (1) for application circumferentially around a patient's limb (10), comprising a) a first band portion (20*a*) and a second band portion (20*b*), both band portions (20) being arrangeable along at least a part of the circumference of the limb for creating radial pressure on the limb, b) a spine element (30), extending in axial direction (100) when the compression device is applied around the limb, and comprising a first and a second guide opening (40*a*, 40*b*) for guiding the first and the second band portions, respectively. The guide openings (40*a*, 40*b*) are arranged offset in axial direction with respect to each other such that, when the first band portion is arranged along at least a part of the circumference of the limb and guided through the first guide opening, and the second band portion is arranged (Continued)

along at least a part of the circumference of the limb, parallel to the first band portion, and guided through the second guide opening, the band portions overlap in an axial direction.

14 Claims, 5 Drawing Sheets

(58) Field of Classification Search
CPC .... A61F 2013/00089; A61F 2013/0093; A61F 2013/00119; A61F 2013/00144
See application file for complete search history.

(56) References Cited

U.S. PATENT DOCUMENTS

| | | |
|---|---|---|
| 5,254,122 A | 10/1993 | Shaw |
| 2003/0149389 A1 | 8/2003 | Daneshvar |
| 2005/0192524 A1* | 9/2005 | Lipshaw ................ A61F 13/06 602/62 |
| 2005/0209545 A1 | 9/2005 | Farrow |
| 2007/0276307 A1 | 11/2007 | Erenstone |
| 2012/0179084 A1 | 7/2012 | Lipshaw |

FOREIGN PATENT DOCUMENTS

| | | |
|---|---|---|
| WO | WO 2004-105657 | 12/2004 |
| WO | WO 2005-092401 | 10/2005 |
| WO | WO 2005/092401 A1 * | 10/2005 |

* cited by examiner

COMPRESSION DEVICE

CROSS REFERENCE TO RELATED APPLICATIONS

This application is a national stage filing under 35 U.S.C. 371 of PCT/US2016/036582, filed Jun. 9, 2016, which claims the benefit of European Application No. 15171126.4, filed Jun. 9, 2015, the disclosures of which are incorporated by reference in their entirety herein.

The invention relates to compression devices useful for treatment of oedema and other venous and lymphatic disorders of a limb of a patient.

Positive effects of compression therapy on venous lymph return as well as on healing of chronic venous ulcers, e.g. venous leg ulcers, are known. Compression bandages and stockings are the most common compression devices used for compression therapy. Compression stockings however often do not provide the desired therapeutic compressive pressure, since such stockings generally need to be quite elastic so that one can pull them on and off. Compression bandages, being made of materials having much lower elastic (or even in some cases nearly non-elastic) characteristics, are typically much more effective than compression stockings in supporting the muscle pump to return venous blood to the heart. Compression bandages however typically need to be applied by a well-trained professional in order to achieve the desired and/or needed fit as well as pressure profile, and such bandages typically need to be reapplied frequently due to change in the volume of the limb (e.g. as a result of oedema reduction).

A number of existing compression devices comprise a compression sleeve and fastening bands or fastening tongues for fixing the sleeve around a patient's limb under tension, so that the bands and/or the sleeve exert pressure on the limb. Depending on the position in which the ends of such bands are fastened, the circumference of the compression device can be adjusted to the size of the patient's limb. Such a device is shown in the patent application U.S. 2005/0192524. It is made of flexible, foldable, light weight Velcro-type loop fabric having a central region for wrapping partially around a body part and a plurality of bands integrally connected to the central region and extending outwardly in opposite directions from both sides of the central region to cross each other and encompass the body part.

A further U.S. patent application, U.S. 2005/0209545, describes an apparatus for applying pressure to a body part comprising multiple interconnectable bands of compressible or noncompressible material. The bands may overlap. Optionally, a spine may be provided to further interconnect the bands.

In the International Patent application WO 2004/105657, which relates to an angiological boot which comprises a compression system which is intended for the ankle and calf region at the lower extremity of the patient suffering from lymphatic or arterial venous insufficiency. In one embodiment, the boot comprises adjustable semi-rigid bands. A plurality of anchoring rectangles, arranged in a row, may be provided.

In certain types of compression devices, bands serve to hold one edge of a compression sleeve to the other end of the sleeve and facilitate adjustment of the size of the compression device to the size of the patient's limb. In many of such devices, the sleeve extends around a major portion of the limb circumference, the bands are comparably short and extend only along a small portion of the circumference of the limb. In other types of compression devices, a sleeve extends only around a small portion of the circumference, i.e. it is narrow, or a sleeve is even not present, and the bands are applied around a larger portion of the circumference of the limb. In these latter compression devices the bands are longer and provide most of the compression.

In both types of compression devices, when applied, an axial gap (i.e. a gap extending in the long direction of the limb) between two adjacent bands is undesirable, because in the area of the gap no pressure is exerted on the limb. Rather, an axial overlap of two adjacent bands is desired for good and complete compression of all axial segments of the limb. The appropriate arrangement of bands is more difficult the longer the bands are, because longer bands get more easily entangled with each other. Generally, compression devices that are difficult to apply are not used as regularly as devices that are easy to apply. Hence, easy and proper axial positioning of the bands during application to the limb, such that adjacent bands have an appropriate axial overlap, is essential for the success of the compression therapy.

The present invention seeks to address this problem. It provides a compression device for application circumferentially around a patient's limb, the limb defining axial, radial and circumferential directions, wherein the compression device comprises a) a first band portion and a second band portion, both band portions being arrangeable along at least a part of the circumference of the limb for creating radial pressure on the limb, b) a spine element, extending in axial direction when the compression device is applied around the limb, and comprising a first guide opening and a second guide opening for guiding the first and the second band portions, respectively, the guide openings being arranged offset in axial direction with respect to each other such that, when the first band portion is arranged along at least a part of the circumference of the limb and guided through the first guide opening, and the second band portion is arranged along at least a part of the circumference of the limb, parallel to the first band portion, and guided through the second guide opening, the first band portion and the second band portion overlap in an axial direction.

The guide openings in the spine element reduce the risk of entanglement of band portions with each other and thereby make application of the compression device easier. The arrangement of the guide openings ensures that adjacent parallel band portions, guided through the guide openings, have an appropriate axial overlap, and thereby reduces the risk of creating gaps between adjacent parallel bands when the compression device is applied.

In the context of this disclosure, the patient's limb defines axial directions (directions parallel to the long direction of the limb), radial directions (directions perpendicular to the axial directions, from or towards the central axis of the limb) and circumferential directions (along the circumference of the limb).

A compression device according to the present invention comprises a first band portion and a second band portion. A compression device may comprise a third band portion and further band portions. A preferred embodiment of the compression device comprises six band portions.

Band portions have a flat, elongate shape, i.e. they extend in a length direction when flat. A distance between side edges of a band portion is a width of the band portion. Width directions are perpendicular to the length direction. A centre line is a virtual line extending in the length direction parallel to the side edges of a band portion and centred between them. A band portion has one or two end portions at opposed ends of the band portion. Band portions may be bendable or comprise bendable portions, i.e. they can be deformed such that they can be bent out of a plane. Generally, a band portion may be bendable such that it can be guided through an opening and be folded back by an angle of 180°, e.g. folded back upon itself. Generally, band portions are easily bendable so that they can conform to the circumference of the limb and can be easily guided through the guide openings.

The first and the second band portions are arrangeable along at least a part of the circumference of the patient's limb, or in other words, they are arrangeable circumferentially around the limb. By arranging the band portions around the limb, e.g. under tension in the length direction, radial pressure on the limb can be created. The radial pressure exerted by the band portions forms the essence of the compression therapy.

The first and the second band portions are arrangeable along at least a part of the circumference of the patient's limb parallel to each other. The first and the second band portions may be arranged along at least a part of the circumference of the patient's limb parallel such that a centre line of the second band portion is offset in an axial direction from a centre line of the first band portion.

The first band portion and the second band portion may overlap in an axial direction, when the compression device is applied around the limb. In other words, an axial portion (a "width" portion) of the first band portion is arranged radially over an axial or "width" portion of the second band portion.

Generally, a band portion may comprise a hook-receptive element or a hook-receptive surface portion. A band portion may be made of hook-receptive material. "Hook" refers to a hook-shaped or mushroom-shaped surface feature, adapted to be used in a mechanical fastening system like, for example, in a Velcro™-type mechanical fastening system. "Hook-receptive" refers to a property of a material to be adapted to engage with hook-shaped or mushroom-shaped surface features in a mechanical fastening system like, for example, in a Velcro™-type mechanical fastening system. A hook-receptive element or a hook-receptive surface portion may comprise so-called loop material. Loop material is material adapted for mechanical engagement with hook material.

Generally, a band portion may comprise a hook-material element or a hook-material surface portion. A band portion may be made of hook-material. "Hook-material" refers to a material comprising hook-shaped or mushroom-shaped surface features, the material being adapted to be engaged with a hook-receptive element, a hook-receptive surface portion, or a hook-receptive material, used in a mechanical fastening system like, for example, in a Velcro™-type mechanical fastening system.

Band portions may be stretchable, e.g. stretchable in their length direction. Band portions may comprise a stretchable material. One or more or all of the band portions may comprise neoprene. One or more or all of the band portions may comprise a laminate of polyester knitted fabric and polyurethane foam, such as those marketed by Rubberlite, Huntington, U.S.A. One or more or all of the band portions may comprise a polyester fabric, such as RP-M-767 or RF-M-2877 manufactured by Green Textiles, Spartanburg, U.S.A.

One or more or all of the band portions may be breathable and/or comprise a breathable material. Such a breathable material may be, for example, Breathoprene available from AccuMed Innovative Technologies.

The compression device according to the invention may comprise a central portion. The first band portion and/or the second band portion may originate from the central portion. In other words, a band portion may be a single piece with the central portion. The central portion may comprise protrusions forming the first band portion and the second band portion. Similarly, a third band portion and/or the fourth band portion and/or any further band portion may originate from the central portion.

Alternatively, the first band portion and/or the second band portion may be connected with the central portion. Generally, a connection between a band portion and the central portion may be releasable and/or re-attachable.

The compression device comprises a spine element, extending in axial direction when the compression device is applied around the limb. The spine element may have an elongate shape, defining a long axis of the spine element. Relative to the limb, the spine element may be arranged such that its long axis is oriented parallel to the axial direction of the limb. The band portions may then be arranged such that their centre lines are perpendicular to the long axis of the spine element, when the compression device is applied around the limb.

The spine element comprises a first and a second guide opening for guiding the first and the second band portions, respectively. In other words, the spine element comprises a first guide opening for guiding the first band portion, and a second guide opening for guiding the second band portion.

A guide opening may be adapted to guide a band portion in axial direction or in radial direction or both, wherein axial and radial directions refer to a situation where the compression device is applied to the limb.

Guiding of a band portion means maintaining a position of the band portion in axial and/or radial directions, and restraining movement of the band portion in axial and/or radial directions before, during and after the band portion is moved through, or threaded through, the guide opening in a length direction of the band portion. A band portion may be guided by a guide opening when the band portion is moving through the guide opening, e.g. moving in a circumferential direction, and/or when the band portion is stationary with respect to the guide opening.

A guide opening may guide a single band portion or two band portions. A band portion may be guided by a single guide opening. A guide opening may guide a band portion that is passing through the guide opening.

Guidance of the band portions provides the advantage that, in the vicinity of the spine element, the arrangement of band portions relative to each other may be determined by the arrangement of the guide openings which guide these band portions. In a compression device according to the invention, a suitable arrangement of guide openings may result in band portions having a desired amount of overlap in an axial direction and, in particular, may result in avoiding the creation of axial gaps between band portions, at least in the vicinity of the spine element.

The first and the second guide opening may be arranged next to each other in the spine element. They may be arranged offset in an axial direction with respect to each other. "Offset in an axial direction" means that a geometric centre point of the first guide opening is at a different axial position than a geometric centre point of the second guide opening.

The first and the second guide openings may be arranged offset in a circumferential direction with respect to each other. "Offset in a circumferential direction" means that the geometric centre point of the first guide opening is at a different circumferential position than the geometric centre point of the second guide opening.

Any guide opening, and in particular at least one of the first and the second guide opening, may be adapted to allow fixation of a band portion, guided through the at least one guide opening, on the band portion itself. The first guide opening may thus, for example, be adapted such that the first band portion can be guided through the first guide opening and then be folded back in order for the folded-back portion to contact a non-folded-back portion of the band portion and be fixed to that non-folded-back portion. A guide opening may, for example, be formed by a thin rim delimiting the guide opening, over which rim the band portion may be folded back.

Generally, a band portion may have first and second end portions at opposed longitudinal ends of the band portion. A first end portion of any band portion, in particular of the first and/or the second band portion, may be permanently connected to the spine element. The first end portion and the spine element may be a single piece, whereby the first end portion of the band portion is permanently connected to the spine element.

Alternatively, the first end portion and the spine element may be different elements. In that latter case the first end portion of any band portion, in particular of the first and/or the second band portion, may be permanently or releasably connected to the spine element.

An opposed second end portion of any band portion, in particular of the first band portion, may be guidable through the first guide opening. It may be adapted to be guided through the first guide opening, for example by adapting the shape or the thickness of the second end portion.

In a specific embodiment of the invention, the first end portion of the first band portion is permanently connected to the spine element, and the second end portion of the first band portion is guided through the first guide opening. This allows the first band portion to be connected to the spine element at its first end portion, an intermediate portion of the band portion (between the end portions) to be arranged along the circumference of the limb, and the second end portion to be guided through the first guide opening. Thereby, the first band portion may be properly positioned around the limb. By being guided through the first guide opening, it may also be adjustable in length direction, in order to adjust the circumference of the compression device to the circumference of the patient's limb.

Generally, the spine element may be rigid. I other words, it may be stiff. A rigid or stiff spine element has some resistance to bending. Generally, a spine element may be resistant to elastic deformation. In other words, considerable force is required to change its shape elastically.

For example, a specific band portion exerting a pull force of 100 Newton on the spine element in circumferential direction when guided through a guide opening, should preferably not cause a displacement of more than 1-2 mm of this guide opening relative to its original circumferential position without pull force, when the compression device is in use and all other band portions are permanently connected to the spine element and are guided through corresponding guide openings under tension and create pressure on the limb.

In order to obtain a suitable stiffness or rigidity of the spine element, a material of the spine element may be chosen for which the elasticity modulus for bending the spine element in a direction perpendicular to its long direction is higher than 1500 N/mm$^2$ (as measured according to DIN 53457), and is preferably higher than 3000 N/mm$^2$.

Generally, a rigid or stiff spine element keeps its overall shape when band portions pull different portions of the spine element into different directions. In particular, it keeps its shape when the first band portion pulls one portion of the spine element into one circumferential direction and a the second band portion pulls an adjacent portion of the spine element into an opposite circumferential direction. A rigid or stiff spine element may keep the first guide opening and the second guide opening in a defined spatial relation to each other when the spine element is exposed to mechanical forces. A rigid or stiff spine element may thus keep band portions in their proper position before, during and/or after application of the compression device around the patient's limb.

The spine element may be a single piece. In other words, the spine element is made from a single piece of material when it is manufactured. An example is a spine element cast as a single piece of polymeric material, or a spine element machined out of a single piece of metal. Single-piece spine elements may provide a higher mechanical stability and/or may provide a higher rigidity, so that the position of guide openings is better maintained when the band portions are tensioned in order to exert therapeutic pressure on the limb.

The spine element may have an elongated shape. Its long extension may be in axial direction when the compression device is applied to the limb. The spine element may, for example, have the shape of a rod, e.g. a rod with a flat cross section. Guide openings may then be arranged in the spine element offset from each other in the direction of the long extension of the spine element. A spine element having an elongated shape, its long extension being in axial direction when the compression device is applied to the limb, may be beneficial in that it may provide guide openings for a greater number of band portions. In specific embodiments, it may also occupy less space in circumferential direction of the limb, which in turn may allow a greater portion of the band portions to contact the limb and to compress it. Also, compression by band portions is often more effective and more comfortable for the patient than compression by a spine element, in particular, if the spine element is rigid.

Generally, and independent from other features, the spine element may comprise one half of a zipper for attaching an extension element to the spine element. The one half of the zipper may be arranged close to an edge of the spine element in a circumferential direction.

The extension element may comprise another half of the zipper, corresponding to, i.e. matching with, the one half of the zipper comprised in the spine element. The two halves of the zipper can be engaged with each other for attaching the extension element to the spine element. Once attached, the two halves of the zipper can later be disengaged from each other for separating the extension element from the spine element.

The extension element may comprise one or more surface portions that are adapted to be engageable with a corresponding mechanical fastening surface. It may, for example, comprise a hook-type surface portion that is adapted to be engageable with a corresponding hook-receptive, i.e. loop-type surface portion, e.g. a loop-type surface portion comprised in a band portion. It may, for example, comprise a hook-receptive, loop-type surface portion that is adapted to be engageable with a corresponding hook-type surface portion, e.g. a hook-type surface portion comprised in a band portion. Such surface portions of the extension element may facilitate easy and quick fixation and/or disengagement of band portions to/from the extension element, e.g. manual fixation or manual disengagement.

The extension element may be stiffer than any one of the band portions. The extension element may consist of a material which has a modulus and/or stretching behaviour which is different from the modulus or stretching behaviour of any one band portion. A stiffer extension element may facilitate handling of the compression device as a whole. It may also be easier to attach to the spine element.

The extension element may comprise, for example, a support element, to which respective first end portions of the first and of the second band portion are affixed, such that respective second end portions of the first and of the second band portion can be guided through the guide openings and/or can be affixed to the spine element. The compression device may be opened by separating the extension element from the spine element by disengaging the two halves of the zipper. The opened compression device may be applied easily about the patient's limb without tension. The extension element can then be attached to the spine element by engaging the two halves of the zipper with each other, whereby the compression device is closed.

The closed compression device may exert compressive force on the patient's limb right after closing the zipper, if the band portions were in a tight configuration before opening the zipper. Alternatively, the closed compression device may not yet exert compressive force on the patient's limb right after closing, if the band portions were in a loose configuration before closing the zipper. In the latter case, the band portions may be tightened after closing of the compression device, in order to exert therapeutic pressure on the patient's limb.

Generally, the guide openings may have center points that are offset relative to each other in axial direction. In other words, the center points may be offset relative to each other in axial direction when the compression device is applied to the limb. For a spine element having an elongated shape, the guide openings may be offset from each other in the direction of the long extension of the spine element. The offset arrangement allows for proper positioning of the first and second band portions guided by the guide openings. In particular, it may allow to avoid gaps in axial direction between adjacent band portions, at least in the vicinity of the guide openings. The offset arrangement of the center points of the guide openings may allow for a staggered arrangement of the guide openings. In particular, it may allow to avoid gaps in axial direction between adjacent band portions, at least in the vicinity of the guide openings.

A center point of a guide opening, in the context of this disclosure, is the geometric center of the guide opening projected in a plane. If the guide opening is not symmetric, the center point is the virtual "center of gravity" of a disc having the size and shape of the guide opening projected in a plane.

The guide openings may overlap in axial direction. They may overlap in axial direction when the compression device is applied to the limb. This is to say that the axial extension of a first guide opening and the axial extension of a second guide opening have a common axial area. An overlap in axial direction may ensure that adjacent band portions guided through the guide openings overlap in axial direction. This may help avoid axial gaps between two adjacent band portions, which in turn may provide for more effective therapeutic compression.

Generally, guide openings are separate from each other. An overlap of two guide openings in axial direction (an "axial overlap") may be achieved by arranging the two guide openings in the spine element both with an offset in axial direction and an offset in circumferential direction.

Independent of any axial overlap of two guide openings and any other features, two guide openings in the spine element may be arranged offset in radial direction with respect to each other. Specifically, one guide opening may be arranged radially outward of the other guide opening, axially offset or not. In general terms, at least a portion of the second guide opening may be arranged radially outward from at least a portion of the first guide opening, when the compression device is applied to the limb. Such an arrangement may be advantageous in order to guide respective band portions through the guide openings with less risk of entanglement between the band portions. Such an arrangement may also facilitate tightening or loosening or fixation of the outer band portion without affecting the inner band portion.

The first guide opening and/or the second guide opening may have the shape of an elongated slit. Band portions that have a flat cross section may be efficiently guided by such slit-shaped guide openings. This may save space on the spine element. Generally, a guide opening may have a shape of the cross section of the band portion that is to be guided by the guide opening. Such a shape may reduce the risk of a band portion getting entangled in the guide opening guiding it.

Where the first guide opening and/or the second guide opening has the shape of an elongated slit, the long direction of the slit may be oriented in axial direction, when the compression device is applied to the limb. The long direction of the slit may be oriented in the long direction of an elongated spine element. This orientation of a slit may be particularly space-saving on the spine element.

Generally, the spine element may further comprises a third guide opening for guiding a third band portion. The third guide opening may be arranged offset in axial direction with respect to the second guide opening, such that, when the second band portion is arranged along at least a part of the circumference of the limb and guided through the second guide opening, and the third band portion is arranged along at least a part of the circumference of the limb, parallel to the second band portion, and guided through the third guide opening, the second band portion and the third band portion overlap in an axial direction. More guide openings allow for more band portions to be guided and supported by the guide openings. More band portions, in turn, may allow for a more location-specific amount of therapeutic pressure exerted by respective band portions.

The spine element may comprise two or more further guide openings, wherein the first and the second guide opening and the further guide openings may be arranged in two parallel rows of guide openings. Four guide openings may be arranged in two rows, e.g. in a first row and in a second row. Generally, the two rows may be arranged parallel to each other. Generally, each of the rows may be arranged in axial direction, when the compression device is applied to the limb. A row-type arrangement of guide openings may save space on the spine element, so that the spine element can be smaller. A row-type arrangement may also allow for easier handling of the band portions.

The second row of guide openings may be arranged radially outward of the first row of guide openings, i.e. radially outward when the compression device is applied to the limb.

Generally, the second row of guide openings may be arranged offset in a circumferential direction from the first row of guide openings, i.e. offset in a circumferential direction when the compression device is applied to the limb.

A guide opening in the first row may overlap with a guide opening in the second row in axial direction, i.e. may overlap in axial direction when the compression device is applied to the limb. In particular, each guide opening in the first row may overlap with a guide opening in the second row in axial direction, i.e. may overlap in axial direction when the compression device is applied to the limb.

In such an arrangement, guide openings of a second row, radially outward of the guide openings of a first row, may be arranged axially offset from respective guide openings of the first row.

Such arrangements may be particularly space saving, thereby making it possible to have a smaller spine element. An overlapping arrangement of the guide openings may allow for appropriate positioning of band portions guided by the guide openings, which in turn may help avoid axial gaps between adjacent band portions.

In a compression device comprising guide openings arranged in two parallel rows, the two rows may extend in axial direction and may be spaced from each other in circumferential direction. Such arrangements may guide certain band portions more effectively. Radially-outer band portions that are overlying radially-inner band portions may be guided better by guide openings that are arranged circumferentially spaced from guide openings that guide the radially-inner band portions.

Alternatively, the second row of guide openings may be arranged radially outward of the first row of guide openings, i.e. radially outward when the compression device is applied to the limb. The two rows may be offset with respect to each other in radial direction.

Such arrangements may guide certain band portions more effectively. Radially-outer band portions that are overlying radially-inner band portions may be guided better by guide openings that are arranged radially outward of guide openings that guide the radially-inner band portions. Also, this arrangement may allow for a space-saving design of the spine element and/or a smaller spine element.

The invention will now be described in more detail with reference to the following Figures exemplifying particular embodiments of the invention.

Herein below various embodiments of the present invention are described and shown in the drawings wherein like elements are provided with the same reference numbers.

Figure 1:
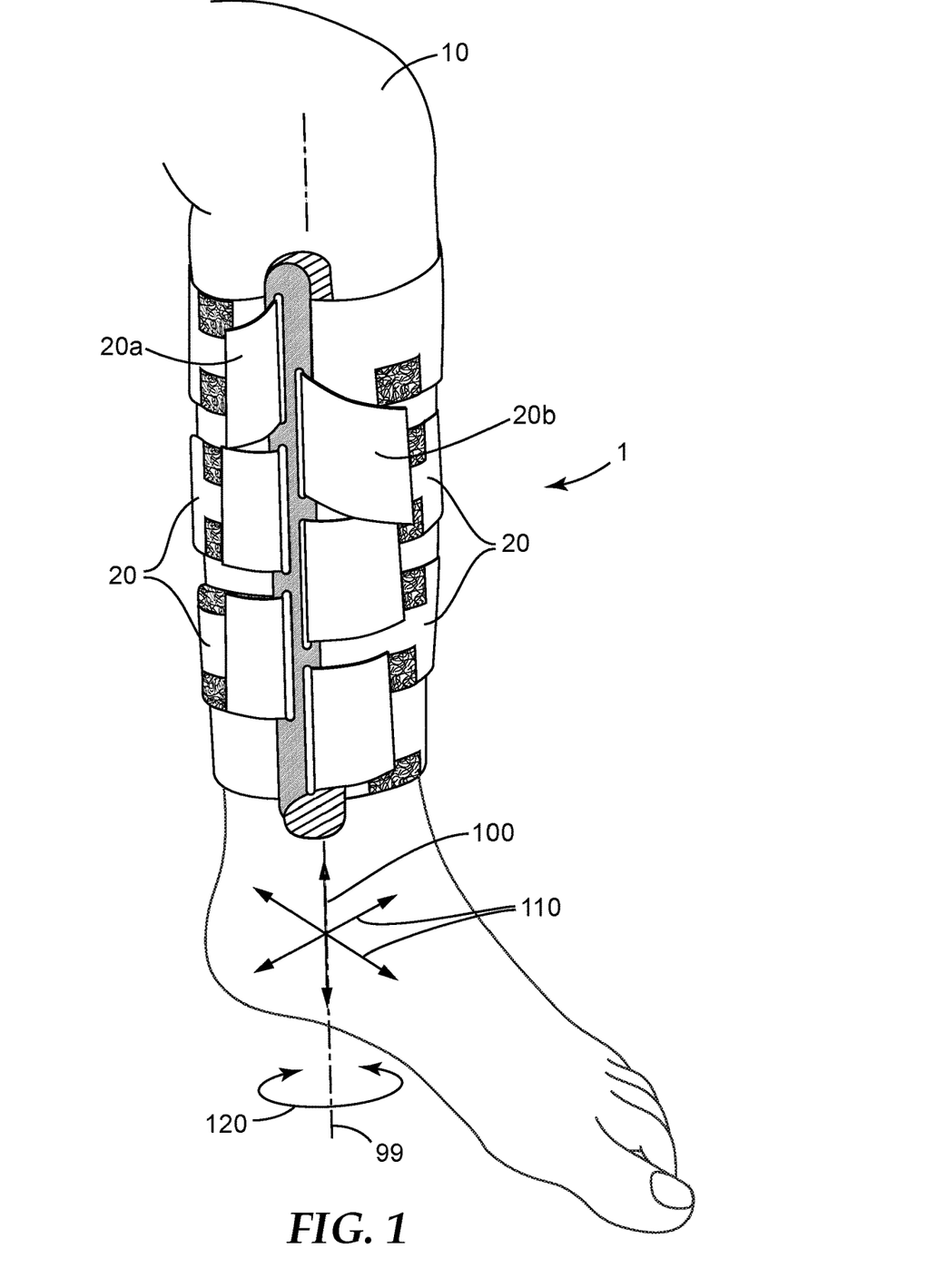
FIG. 1 Perspective view of a first compression device according to the present disclosure, partially applied around a patient's lower leg.

FIG. 1 shows, in a sketched perspective view, a patient's limb 10, a leg, with a first compression device 1 according to the present disclosure, partially applied around the lower leg. The compression device 1 comprises six band portions 20, arranged along the circumference of the limb 10.

The limb 10, around which the compression device 1 is to be applied, defines axial directions 100, which are directions parallel to a central axis 99 of the limb 10, and radial directions 110, which are directions perpendicular to the axial directions 100, from or towards the central axis 99. The limb 10 also defines circumferential directions 120, which are directions along the circumference of the limb 10. When explaining a compression device, a reference to a direction is meant to refer to the direction when the compression device is applied to a patient's limb 10 in a way shown in FIG. 1, i.e. in a normal way.

The band portions 20 are elastic, i.e. they can be stretched in their length direction and strive to return to their original length. They comprise an elastic material. Elastic band portions 20 may, for example, comprise a) a laminate of polyester knitted fabric and polyurethane foam, such as those marketed by Rubberlite, Huntington, U.S.A., b) polyester fabric, such as RP-M-767 or RF-M-2877 manufactured by Green Textiles, Spartanburg, U.S.A., c) Breathoprene, available from AccuMed Innovative Technologies, or d) AirFlex 2, available from Eastex Products Inc., Holbrook, Mass.

The stretch behavior of the elastic material is preferably selected such, that the elongation of a band portion 20, when exposed to a longitudinal (along-band) force of 10N per 1 cm width of the band portion is more than 5%; but less than 40%, and preferably is less than 20%.

Also, an axial overlap of two band portions 20 should not cause significant indents on the skin. Therefore, preferably, a band portion 20 is compressible and/or soft. For the same reason, preferably, a band portion 20 is thin, e.g. has a thickness of less than 2 mm, preferably less than 1 mm, and more preferably less than 0.5 mm.

The band portions 20 can be stretched or expanded elastically in circumferential directions 120. They are applied under tension circumferentially around the limb 10 and are affixed under tension such that each band portion 20 exerts radial pressure on the limb 10. This radial pressure is the therapeutic pressure.

The compression device 1 is only partially applied to the limb 10: The two uppermost band portions 20a and 20b shown in FIG. 1 are shown before fixation. Hence these band portions 20a, 20b do not exert radial pressure on the limb 10. Once these band portions 20a, 20b are affixed under tension and exert pressure, the compression device 1 is completely applied around the limb 10.

Figure 2:
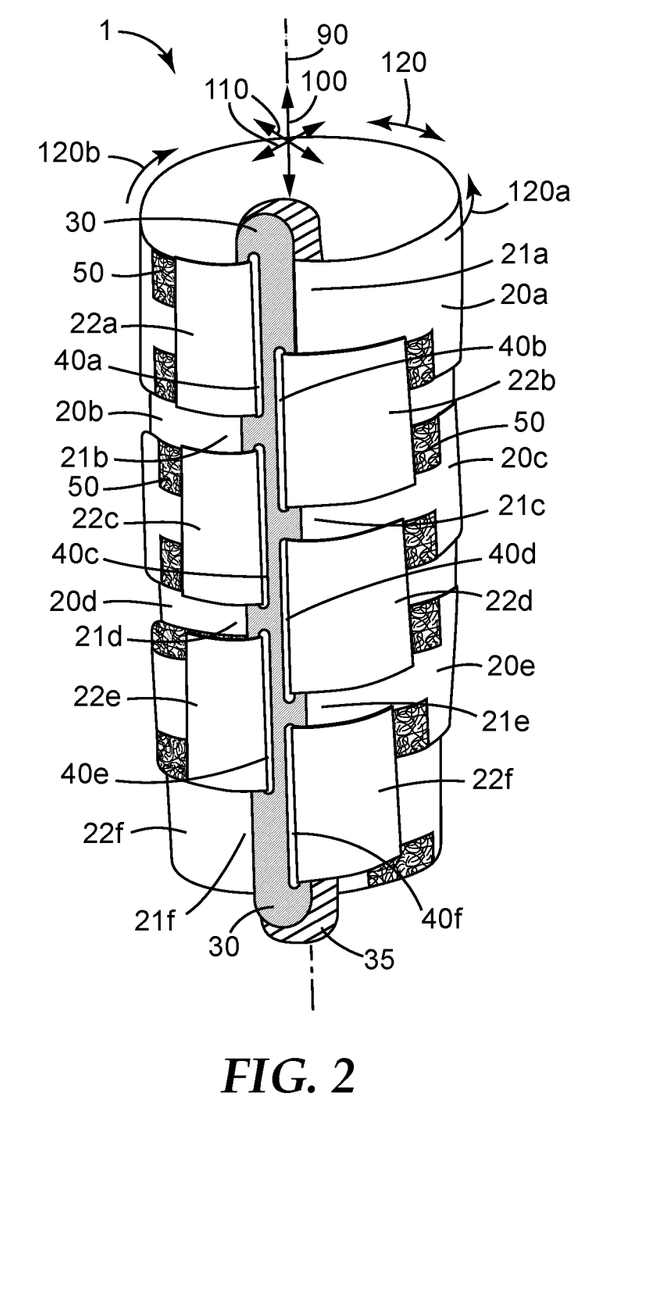
FIG. 2 Perspective front view of the first compression device.

FIG. 2 shows, in a perspective front view, the first compression device 1 in greater detail in its fully applied state. The limb 10 is not shown, for greater clarity. Six band portions 20a, 20b, 20c, 20d, 20e, 20f, are applied along the circumference of the limb 10. Each of the band portions 20a, 20b, 20c, 20d, 20e, 20f is permanently attached to a rigid spine element 30, that has an elongated shape. Its long extension is oriented in axial direction 100.

Figure 4:
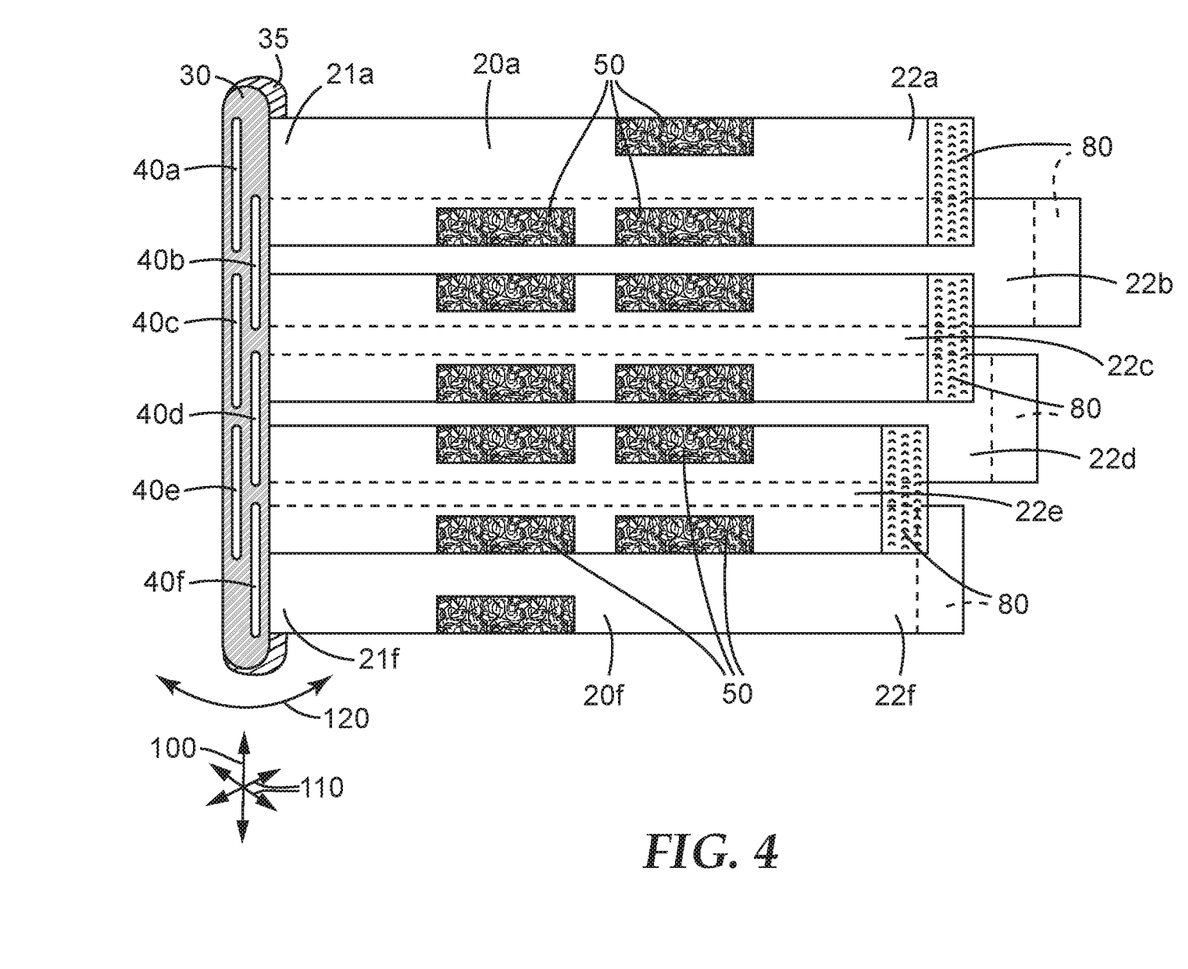
FIG. 4 Plan view of the first compression device.

The band portion 20a has a first end portion 21a, which is permanently attached or connected to the spine element 30, and an opposed second end portion 22a, which is guided through a first guide opening 40a of the spine element 30. The second end portion 22a passes through the first guide opening 40a and is folded back upon the band portion 20a. The second end portion 22a is releasably affixed to the band portion 20a by two fixation patches 50, arranged on the radially outer surface of the band portion 20a. The folded-back second end portion 22a can mechanically engage with the fixation patches 50, and is thereby releasably affixed to the band portion 20a and held in place under tension. Specifically, the fixation patches 50 comprise so-called loop material that can mechanically engage with so-called hook material on the end portion 22a. Fixation patches 50 can be mechanically engaged with corresponding fixation areas 80

(shown in FIG. 4) comprising hook material. These fixation areas 80 are arranged on the respective end portions 22a-f of the band portions 20a-f. Fixation areas 80 can be released or disengaged from the fixation patches 50 manually. The fixation areas 80 and the fixation patches 50 thus facilitate releasable fixation of band portions 20.

All other band portions 20b, 20c, 20d, 20e, 20f are similar to the band portion 20a described in the preceding paragraph and will therefore not be described separately.

One difference, however, is that three band portions, namely the band portions 20a, 20c, and 20e, extend along the circumference of the limb 10 in one circumferential direction 120, namely in a counter-clockwise circumferential direction 120a from their first end portions 21a, 21c, 21e to their respective second end portions 22a, 22c, 22e when viewed from above. The remaining three band portions, namely the band portions 20b, 20d, and 20f, extend along the circumference of the limb in the opposite circumferential direction 120, namely in a clockwise circumferential direction 120b from their first end portions 21b, 21d, 21f to their second end portions 22b, 22d, 22f, when viewed from above.

A cushioning element 35 extends along the side of the spine element 30, where the first end portions of band portions 20a, 20c, 20e are connected to the spine element 30. The cushioning element 35 comprises a resilient foam material. It helps reduce impressions into the skin that might be caused by the spine element 30, and in particular by its edges, when the compression device 1 is fully applied and the tensioned band portions 20 pull the spine element 30 radially onto the skin of the limb 10.

Band portion 20a and band portion 20b are adjacent band portions, because the band portion 20a is the first band portion, and band portion 20b is the second band portion, counted from the top of the compression device. Similarly, band portion 20b and band portion 20c are adjacent band portions, because band portion 20b is the second band portion, and band portion 20c is the third band portion, counted from the top of the compression device 1. Adjacent band portions 20 are thus defined by their "position count" relative to the top of the compression device 1.

Going from the topmost band portion 20a to the bottom band portion 20f, the direction in which the band portions 20 extend from their respective permanently attached first end portions 21 to their respective second end portions 22 alternates from band portion to band portion between counter-clockwise and clockwise circumferential extension along the circumference of the limb 10. Adjacent band portions 20 thus extend circumferentially in opposed circumferential directions 120, when the compression device 1 is applied around the limb 10. This alternating arrangement helps to obtain a balanced distribution of tension forces on the spine element 30, which makes it easier to keep the spine element 30 in place relative to the limb 10.

In the embodiment of a compression sleeve according to the present disclosure shown in FIGS. 1 and 2, adjacent band portions 20 overlap in axial direction 100. For example, the uppermost band portion 20a overlaps the adjacent band portion 20b, i.e. it is arranged, when the compression device 1 is fully applied, radially outward of the adjacent, second band portion 20b and on the outer surface of the second band portion 20b (except where the second end portion 22b of the second band portion 20b is folded back upon itself and upon a part of the first band portion 20a).

The length of a band portion 20 is defined by its extension in circumferential direction 120, its width by its extension in axial direction 100. About 30 percent of the width of the second band portion 20b, namely the upper 30 percent, are covered by the first band portion 20a. In other words, there is a 30 percent overlap in axial direction (or "axial overlap") of the second band portion 20b with the first band portion 20a. This axial overlap between adjacent band portions 20 ensures that axial gaps between adjacent band portions 20 can normally not occur. An axial gap between adjacent band portions 20 might create an area on the limb 10 on which no radial pressure is exerted by the compression device 1. A smaller amount than 30% of axial overlap is possible, but generally a smaller amount of axial overlap increases the risk of axial gaps between adjacent band portions 20. A greater amount of overlap than 30% is possible, but generally a greater amount of axial overlap tends to make the compression device 1 heavier and more awkward to apply, because wider band portions 20 and/or more band portions 20 need to be present and need to be managed.

A similar axial overlap as described above for band portions 20a and 20b exists between the other adjacent band portions 20 of the compression device 1.

Due to the axial overlap, the folded-back second end portion 22b of the second band portion 20b touches the first band portion 20a, the second band portion 20b, and the third band portion 20c. Fixation patches 50 for releasably affixing the second end portion 22b of the second band portion 20b are arranged on the radially outer surfaces of the first band portion 20a and of the third band portion 20c, respectively. Fixation patches 50 for fixating band portions 20 arranged axially between two other adjacent band portions 20 may thus be arranged on those other adjacent band portions 20.

The band portions 20 of the first compression device 1 are guided by respective guide openings 40 in the spine element 30. The spine element 30 comprises six guide openings 40. The uppermost band portion 20a is guided by the uppermost guide opening 40a, the next-lower band portion 20b is guided by the next-lower guide opening 40b, and so on for all band portions 20.

Generally, at least a portion of a band portion 20 can be threaded through a guide opening 40. Once threaded, the band portion can be pulled through the guide opening 40, e.g. in order to tension the band portion 20 for applying radial pressure on the limb 10.

In the compression device shown in FIG. 2, the spine element 30 is adapted such that a band portion 20 can be guided by the guide opening 40 and a part of the band portion 20 already threaded through the guide opening 40 can be folded back upon itself, e.g. for releasable fixation of the band portion 20 in a tensioned state.

Figure 3:
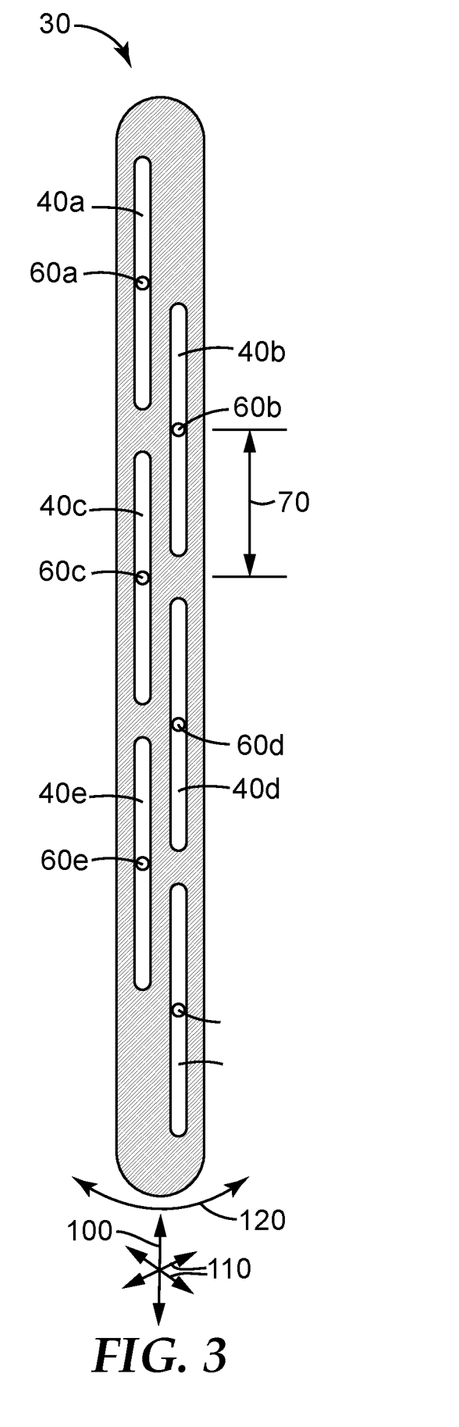
FIG. 3 Plan view of the spine element of the first compression device.

The spine element 30 of the compression device 1 shown in FIGS. 1 and 2 is shown in more detail and without band portions 20 in a plan view in FIG. 3. The spine element 30 has an elongated shape and its long extension is oriented in axial direction 100 when the compression device 1 is applied around the limb 10. The spine element 30 is rigid. It is made of polyamide. It may alternatively be made of, for example, metal, reinforced or non-reinforced polymers such as polyester, polycarbonate, Acryl-Butadien-Styrol copolymer, polypropylene, polycarbonate, polyethersulfone or polyvinylchloride.

All guide openings 40 have an identical shape, namely the shape of an elongated slit. The long direction of the slit is oriented in axial direction 100, when the compression device 1 is applied around the limb 10. In other words, their long directions are oriented in the long direction of the spine element 30. In other embodiments, guide openings 40 may have different shapes, and one guide opening 40 may have a different shape than another guide opening 40. Generally, it is preferable if the shape of a guide opening 40 corresponds to the cross section of a band portion 20 which is to be guided by the guide opening 40. The shape of a guide opening 40 is preferably selected such that the band portion 20 can be conveniently manually threaded into and pulled through the guide opening 40.

Each guide opening 40 defines a center point 60, which is defined as the geometric center of the guide opening 40, projected in a plane. The center point 60 of the uppermost guide opening 40a is indicated as 60a in FIG. 3, the center points 60 of the other guide openings 40b, 40c, etc. are indicated correspondingly as 60b, 60c, etc.

Any two guide openings 40 are offset from each other in axial direction 100. In particular, two adjacent guide openings 40 are offset from each other in axial direction 100. That is to say, their center points 60 are on different positions in axial direction 100, i.e. in different axial positions. For example, guide opening 40b and guide opening 40c are adjacent to each other. The center point 60b of guide opening 40b is offset in axial direction 100 from the center point 60c of guide opening 40c by a distance indicated by arrow 70. These two guide openings 40b, 40c are thus considered offset from each other in axial direction 100, or axially offset from each other.

The guide openings 40 restrict axial and radial movement of the band portions 20 guided by them such, that the axial (along-limb) position and the radial (outward distance from limb) position of the band portions 20 is kept and maintained, both when pulling band portions 20 through their respective guide openings 40, and when the band portions 20 are not moving with respect to their respective guide openings 40.

Axial overlap of adjacent guide openings 40 leads to an axial overlap of band portions 20 that are guided by the guide openings 40. This overlap of the band portions 20 is present at least in the vicinity of the spine element 30. For two band portions 20 guided by overlapping adjacent guide openings 40, that are arranged along the circumference of the limb 10 in a normal manner, i.e. parallel to each other, the axial overlap of these band portions 20 is present along the entire circumference of the limb 10.

In the compression device 1 shown in FIGS. 1 and 2, a first end portion 21 of the band portions 20 are permanently connected to the spine element 30. This permanent connection may be done in different manners, e.g. adhesively, by welding or sowing. For each band portion 20, the axial position, in which the first end portion 21 is connected to the spine element 30, is the same axial position in which the second end portion 22 is guided by the guide opening 40. This results in the band portions 20 being arranged along the circumference of the limb 10 parallel to each other and in a direction perpendicular to the long direction of the spine element 30, i.e. perpendicular to the axial direction 100 and thereby purely in a circumferential direction 120. This arrangement of the band portions 20 facilitates easy, quick and orderly application of the compression device 1 around the limb 10.

FIG. 4 shows the compression device 1 of FIGS. 1 and 2, in plan view, when laid out flat. The arrangement of the fixation patches 50, arranged on the radially outer surface of the band portions 20. The fixation patches 50 comprise loop material, i.e. hook-receptive material. They can mechanically engage with fixation areas 80, which comprise hook material on the second end portions 22 of the band portions 20. Fixation areas 80 on every other band portion, namely on band portions 20b, 20d and 20 f, are not visible in FIG. 4, because they are arranged on the underside surfaces of the band portions 20b, 20d, 20f.

It may be worth noting that some band portions 20 comprise fixation patches 50 for releasably affixing not, or not only, the band portion 20 itself, but also for releasably affixing one or two adjacent band portions 20.

Figure 5:
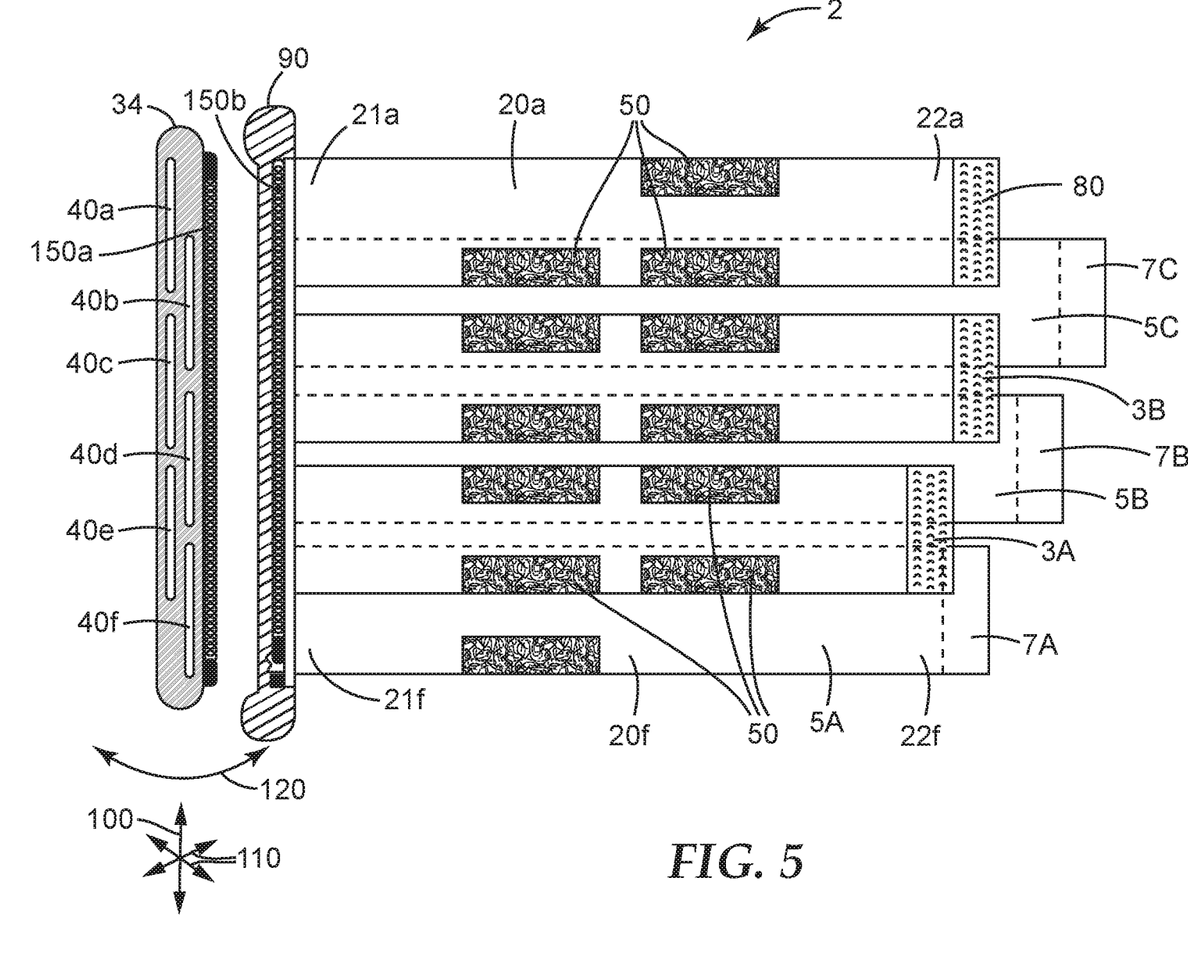
FIG. 5 Plan view of a second compression device according to the present disclosure, comprising a zipper.

An alternative, second compression device 2 according to the invention is shown in FIG. 5 in plan view, laid out flat. The second compression device 2 is identical to the first compression device 1 except that the first end portions 21 of band portions 20 are permanently connected not to the spine element 31 directly, but to an extension element 90 which can be attached to the spine element 31 and separated from it by a zipper 150. The zipper 150 comprises a first half 150a and a matching second half 150b. The first half 150a of the zipper 150 is comprised in the spine element 31, the second half 150b of the zipper 150 is comprised in the extension element 90. The first half 150a of the zipper 150 is arranged at a side edge (i.e. an edge in circumferential direction 120) of the spine element 31. It extends parallel to the long direction of the spine element 31, i.e. in axial direction 100, when the compression device 2 is applied around the limb 10.

When the compression device 2 is in use and is applied around a patient's limb 10, band portions 20b, 20d and 20f are arranged similarly to what is shown in FIG. 2. In use, these band portions 20b, 20d and 20f cover the zipper 150. In order to open the zipper 150, end portions 22b, 22d, 22f of those band portions 20b, 20d and 20f must be disengaged from the fixation patches 50 to which they are engaged when in use, and folded back to some degree in order to make the zipper 150 accessible. The band portions 20b, 20d and 20f do not need to be unthreaded from their respective guide openings 40b, 40d, 40f for the zipper 150 to be accessible. The other band portions 20a, 20c, 20e do not obstruct access to the zipper 150 when in use, and can remain in place, their end portions 22a, 22c, 22e can remain engaged with the corresponding fixation patches 50.

Once band portions 20b, 20d and 20f have been disengaged from their fixation patches 50 and folded back to a sufficient degree, the zipper 150 can be opened. Opening the zipper 150 opens the compression device 2 completely without unthreading the band portions 20 from the guide openings 40. The compression device 2 can then easily be removed from the limb 10. Similarly, the compression device 2 can be put on again without having to thread any band portions 20 into their corresponding guide openings 40. This makes it easier and quicker to put the compression device 2 around the limb 10 and to remove it from the limb 10.

Figure 6:
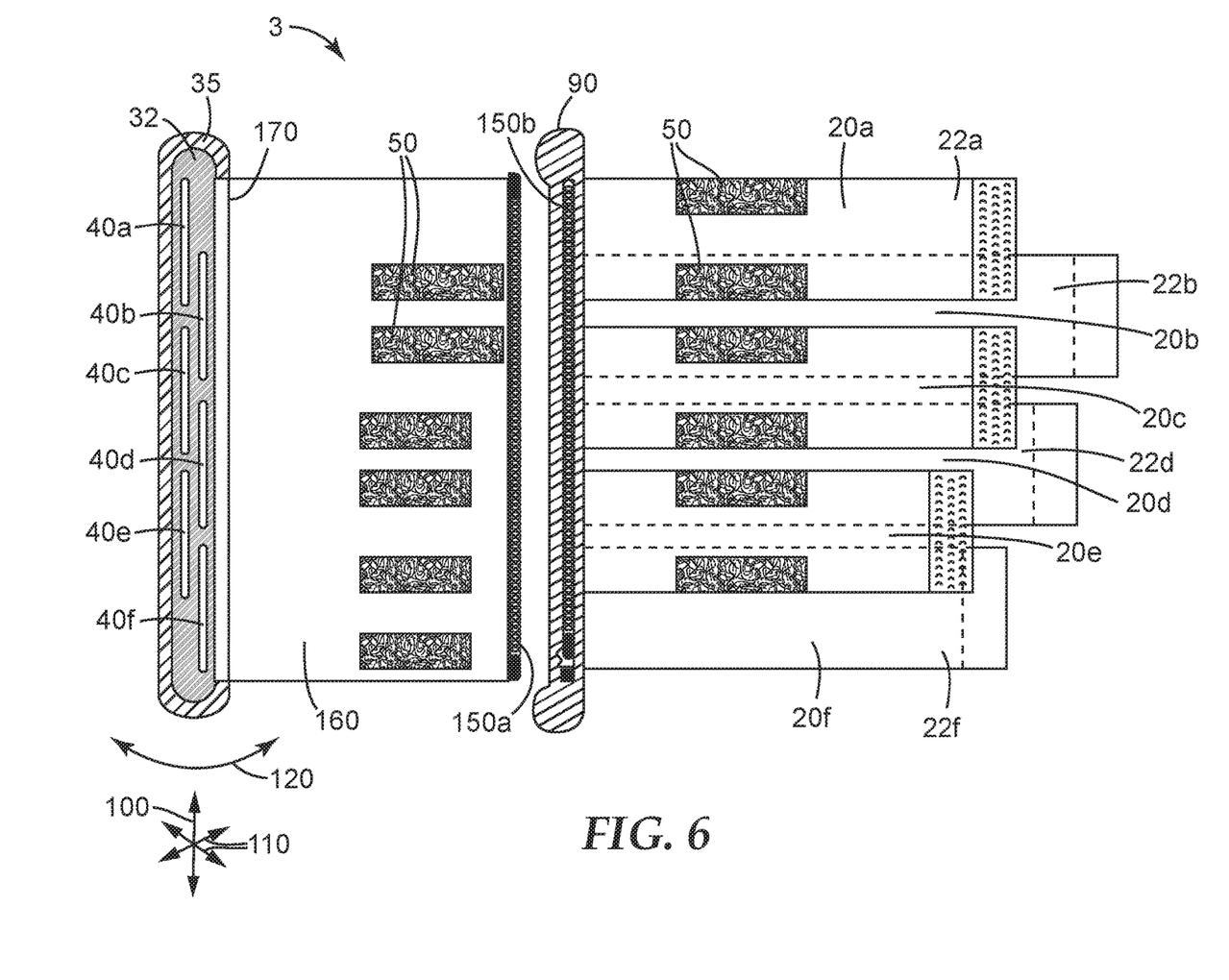
FIG. 6 Plan view of a third compression device according to the present disclosure, comprising a zipper and an extension element.

In an alternative, third compression device 3 according to the invention is shown in FIG. 6 in plan view, laid out flat. It is identical to the second compression device 2, except that the extension element 90 is not connectable, via a zipper 150, to the spine element 32 directly. Rather, the first half 150a of the zipper 150 is arranged on a side edge of an interface sheet 160, which is permanently connected to the spine element 32 on the left side edge (in the FIG. 170 of the interface sheet 160. The interface sheet 160 is made of a stretchable, elastic material, similar to the material of which the band portions 20 are made. The interface sheet 160 can thereby be arranged circumferentially around the limb and can be tensioned, like the band portions 20, so that it can exert radial pressure on the limb 10. This pressure is therapeutic pressure.

The interface sheet 160 extends, in axial direction 100, about as far as the spine element 32. In the embodiment shown in FIG. 6, the interface sheet 160 has no band structure, but in alternative embodiments it may have a band structure, wherein band portions, similar to the band portions 20a-f, connect the spine element 32 to the first part 150a of the zipper 150.

The interface sheet 160 carries some of the fixation patches 50, while other fixation patches 50 are arranged on the band portions 20a, 20c, 20f.

The extension element 90 comprises the second part 150b of the zipper 150. It can thus be attached indirectly to the spine element 32 (via the interface sheet 160). The zipper 150 allows to detach the extension element 90 from the spine element 32 by detaching the extension element 90 from the interface sheet 160. Band portions 20a-f are permanently connected with the extension element 90 on the (circumferential) side opposite to the side on which the second half 150b of the zipper 150 can be attached to the first half 150a of the zipper 150.

Because the zipper 150 is not arranged directly on the spine element 32 (opposed to what is the case in the embodiment shown in FIG. 5), band portions 20b, 20d, 20f can be arranged around the limb 10, can be guided through the corresponding guide openings 40b, 40d, 40f, can be tensioned to adjust their lengths to the circumference of the limb 10, and are not folded back upon themselves, but are rather attached to the interface sheet 160 at fixation patches 50 located on the interface sheet 160. This fixation keeps the band portions 20b, 20f, 20f under tension, so that they can create therapeutic pressure. Thus when in use, the band portions 20b, 20d, 20f do not cover the zipper 150. Unlike in the second compression device 2 shown in FIG. 5, the zipper 150 remains accessible when the compression device 3 is in use. It is thus not necessary to disengage any of the end portions 22b, 22d, 22f from the fixation patches 50 in order to gain access to the zipper 150. The adjustment of the length of the band portions 20 according to the limb circumference is not lost. Once the zipper 150 is open, the compression device 3 can be removed quickly and easily from the limb 10. It is contemplated that once the compression device 3 has been removed from the limb, the zipper 150 may allow to put the compression device 3 back on the limb without having to re-adjust the length of the band portions 20.

In an alternative embodiment, not shown in the Figures, the entire outer surface of the interface sheet 160 is covered with hook-receptive material, so that fixation areas 80 on the band portions 20 can be releasably attached anywhere on the outer surface of the interface sheet 160. Individual fixation patches 50 can thereby be made obsolete.

Similarly, in any of the compression devices 1, 2 shown in FIG. 1, 2, 4 or 5, the entire outer surface of a band portion 20 may be covered with, or made of, hook-receptive material, so that a fixation area 80 on a band portions 20 can be releasably attached anywhere on the outer surface of the band portion 20. Again, this may make individual fixation patches 50 obsolete.

What is claimed is:

1. Compression device for application circumferentially around a patient's limb, the limb defining axial, radial and circumferential directions, wherein the compression device comprises
   a) a first band portion, a second band portion, and a third band portion, with the first, second, and third band portions being arrangeable along at least a part of the circumference of the limb for creating radial pressure on the limb,
   b) a spine element,
   extending in axial direction when the compression device is applied around the limb, and
   comprising a first guide opening, a second guide opening, and a third guide opening for guiding the first band portion, the second band portion, and the third band portion, respectively,
   wherein the first band portion comprises a first end portion and second end portion, the first end portion is permanently connected to the spine element
   the first, second, and third guide openings being arranged offset in axial direction with respect to each other such that, when the first band portion is arranged along at least a first part of the circumference of the limb and the second end portion of the first band portion is guided through the first guide opening and is folded back onto itself, and the second band portion is arranged along at least a second part of the circumference of the limb, parallel to the first band portion, and guided through the second guide opening, and the third band portion is arranged along at least a third part of the circumference of the limb, parallel to the first band portion and second band portion, and guided through the third guide opening, the second band portion overlaps the first and third band portions in an axial direction; and
   wherein the second band portion releasably affixes to an outer portion of the first band portion and an outer portion of the third band portion.

2. compression device according to claim 1, wherein the first and third band portions extend counter-clockwise in a circumferential direction around the limb, and the second band portion extends clockwise in a circumferential direction around the limb.

3. Compression device according to claim 1, wherein the first and second guide align relative to each other overlap in axial direction.

4. Compression device according to claim 1, wherein the spine element is rigid.

5. Compression device according to claim 1, wherein the spine element is a single piece.

6. Compression device according to claim 1, wherein the spine element has an elongated shape.

7. Compression device according to claim 1, wherein the spine element comprises one half of a zipper for attaching an extension element to the spine element.

8. Compression device according to claim 1, wherein the first and third guide openings have center points that are offset relative to each other in axial direction.

9. Compression device according to claim 1, wherein the first and third band portions each include a fixation patch at an outer surface that releasably affixes with a second end portion of the second band portion.

10. Compression device according to claim 9, wherein the second end portion of the second band portion comprises a fixation area.

11. Compression device according to claim 1, wherein the first guide opening and/or the second guide opening has the shape of an elongated slit.

12. Compression device according to claim 11, wherein the longitudinal length of the elongated slit is oriented in axial direction, when the compression device is applied to the limb.

13. Compression device according to claim 1, wherein the spine element further comprises one or more further guide openings, wherein the first and the second guide openings and the further guide openings are arranged in two parallel rows of guide openings.

14. Compression device according to claim 13, wherein the two parallel rows extend in axial direction and are spaced from each other in circumferential direction.

\* \* \* \* \*

UNITED STATES PATENT AND TRADEMARK OFFICE
CERTIFICATE OF CORRECTION

| | | |
|---|---|---|
| PATENT NO. | : 10,779,994 B2 | Page 1 of 1 |
| APPLICATION NO. | : 15/579959 | |
| DATED | : September 22, 2020 | |
| INVENTOR(S) | : Guido Hitschmann | |

It is certified that error appears in the above-identified patent and that said Letters Patent is hereby corrected as shown below:

In the Specification

Column 14
Line 56             Delete "FIG." and insert -- FIG.) --, therefor.

In the Claims

Column 16
Line 34 (Approx.)   In Claim 3, delete "align relative to each other overlap in" and insert -- openings align relative to each other in --, therefor.
Line 60             In Claim 12, delete "the" (first occurrence) and insert -- a --, therefor.

Signed and Sealed this
Twentieth Day of July, 2021

Drew Hirshfeld
*Performing the Functions and Duties of the*
*Under Secretary of Commerce for Intellectual Property and*
*Director of the United States Patent and Trademark Office*